(12) United States Patent
Savage et al.

(10) Patent No.: US 8,781,576 B2
(45) Date of Patent: Jul. 15, 2014

(54) DEVICE AND METHOD FOR REDUCING PATIENT TRANSTHORACIC IMPEDANCE FOR THE PURPOSE OF DELIVERING A THERAPEUTIC CURRENT

(75) Inventors: Walter T. Savage, Concord, CA (US); Shelley J. Savage, Concord, CA (US); Walter N. Maclay, Sunnyvale, CA (US); Douglas C. Morrison, Union City, CA (US); Thomas K. Geraty, San Jose, CA (US); Mark D. Brinkerhoff, San Jose, CA (US); Ronald S. Boeder, Livermore, CA (US); Tony M. Ton, San Diego, CA (US); Jeffrey S. Greger, Fairfield, CA (US); Peter Gray, Vallejo, CA (US)

(73) Assignee: Cardiothrive, Inc., Concord, CA (US)

( * ) Notice: Subject to any disclaimer, the term of this patent is extended or adjusted under 35 U.S.C. 154(b) by 0 days.

(21) Appl. No.: 13/312,910

(22) Filed: Dec. 6, 2011

(65) Prior Publication Data

US 2012/0310315 A1 Dec. 6, 2012

Related U.S. Application Data

(63) Continuation-in-part of application No. 12/724,269, filed on Mar. 15, 2010, now Pat. No. 8,615,295.

(60) Provisional application No. 61/161,014, filed on Mar. 17, 2009.

(51) Int. Cl.
*A61N 1/38* (2006.01)

(52) U.S. Cl.
USPC .............................................. 607/5

(58) Field of Classification Search
USPC ........................................ 607/4–5, 148, 152
See application file for complete search history.

(56) References Cited

U.S. PATENT DOCUMENTS

| | | | |
|---|---|---|---|
| 5,240,995 A | 8/1993 | Gyory | |
| 5,290,585 A | 3/1994 | Elton | |
| 5,338,490 A | 8/1994 | Dietz | |
| 5,362,420 A | 11/1994 | Itoh | |
| 5,402,884 A | 4/1995 | Gilman et al. | |
| 5,489,624 A | 2/1996 | Kantner | |
| 5,536,768 A | 7/1996 | Kantner | |

(Continued)

FOREIGN PATENT DOCUMENTS

| | | |
|---|---|---|
| DE | 10 2006 025864 | 12/2007 |
| EP | 1 834 622 | 9/2007 |
| WO | WO 03/020362 | 3/2003 |

OTHER PUBLICATIONS

PCT International Search Report of PCT/EP2007/009879; dated Apr. 29, 2008.

(Continued)

*Primary Examiner* — Amanda Patton
(74) *Attorney, Agent, or Firm* — DLA Piper LLP (US)

(57) ABSTRACT

A device and method for reducing patient transthoracic impedance for the purpose of delivering a therapeutic current are provided. In one embodiment, the device for reducing patient transthoracic impedance for the purpose of delivering a therapeutic current may be used in a defibrillator. The device for reducing patient transthoracic impedance for the purpose of delivering a therapeutic current may be a microneedle array that may have a number of different configurations and may be made with different materials.

15 Claims, 18 Drawing Sheets

(56) References Cited

U.S. PATENT DOCUMENTS

| | | | |
|---|---|---|---|
| 5,573,668 A | 11/1996 | Grosh | |
| 5,643,252 A | 7/1997 | Waner et al. | |
| 5,658,316 A | 8/1997 | Lamond et al. | |
| 5,660,178 A | 8/1997 | Kantner | |
| 5,800,685 A | 9/1998 | Perrault | |
| 6,056,738 A | 5/2000 | Marchitto et al. | |
| 6,141,584 A | 10/2000 | Rockwell et al. | |
| 6,197,324 B1 | 3/2001 | Crittenden | |
| 6,251,100 B1 | 6/2001 | Flock et al. | |
| 6,266,563 B1 | 7/2001 | KenKnight et al. | |
| 6,315,722 B1 | 11/2001 | Yaegashi | |
| 6,329,488 B1 | 12/2001 | Terry | |
| 6,379,324 B1* | 4/2002 | Gartstein et al. | 604/22 |
| 6,576,712 B2 | 6/2003 | Feldstein | |
| 6,596,401 B1 | 7/2003 | Terry | |
| 6,597,948 B1 | 7/2003 | Rockwell et al. | |
| 6,611,707 B1 | 8/2003 | Prausnitz | |
| 6,690,959 B2 | 2/2004 | Thompson | |
| 6,714,817 B2 | 3/2004 | Daynes et al. | |
| 6,797,276 B1 | 9/2004 | Glenn | |
| 6,803,420 B2 | 10/2004 | Cleary | |
| 6,908,453 B2 | 6/2005 | Fleming | |
| 6,908,681 B2 | 6/2005 | Terry | |
| 6,931,277 B1 | 8/2005 | Yuzhakov | |
| 7,072,712 B2 | 7/2006 | Kroll et al. | |
| 7,108,681 B2 | 9/2006 | Gartstein | |
| 7,226,439 B2 | 6/2007 | Prausnitz | |
| 7,463,917 B2* | 12/2008 | Martinez | 600/395 |
| 7,645,263 B2* | 1/2010 | Angel et al. | 604/116 |
| 7,797,044 B2 | 9/2010 | Covey et al. | |
| 8,024,037 B2 | 9/2011 | Kumar | |
| 2002/0082644 A1 | 6/2002 | Picardo et al. | |
| 2003/0017743 A1 | 1/2003 | Picardo et al. | |
| 2003/0055460 A1* | 3/2003 | Owen et al. | 607/5 |
| 2003/0167075 A1 | 9/2003 | Fincke | |
| 2003/0197487 A1 | 10/2003 | Tamura et al. | |
| 2004/0105834 A1 | 6/2004 | Singh | |
| 2004/0143297 A1 | 7/2004 | Ramsey | |
| 2004/0166147 A1 | 8/2004 | Lundy | |
| 2004/0247655 A1 | 12/2004 | Asmus | |
| 2005/0123565 A1 | 6/2005 | Subramony | |
| 2006/0136000 A1 | 6/2006 | Bowers | |
| 2006/0142806 A1 | 6/2006 | Katzman et al. | |
| 2006/0206152 A1 | 9/2006 | Covey et al. | |
| 2007/0016268 A1 | 1/2007 | Carter et al. | |
| 2007/0078376 A1 | 4/2007 | Smith | |
| 2007/0150008 A1* | 6/2007 | Jones et al. | 607/3 |
| 2008/0097546 A1 | 4/2008 | Powers et al. | |
| 2010/0063559 A1 | 3/2010 | McIntyre et al. | |
| 2010/0160712 A1 | 6/2010 | Burnett et al. | |
| 2010/0241181 A1* | 9/2010 | Savage et al. | 607/5 |

OTHER PUBLICATIONS

PCT Written Opinion of the International Searching Authority of PCT/EP2007/009879; dated Apr. 29, 2008.

PCT International Preliminary Report on Patentability of PCT/EP2007/009879; dated May 19, 2009.

PCT International Search Report of PCT/US2010/027346; dated Oct. 14, 2010.

PCT Written Opinion of the International Searching Authority of PCT/US2010/027346; dated Oct. 14, 2010.

PCT International Preliminary Report on Patentability of PCT/US2010/027346; dated Sep. 20, 2011.

Extended European Search Report of EP 2408521; dated Jul. 10, 2012.

"Changes in the passive electrical properties of human stratum corneum due electroporation" dated Dec. 7, 1994. By U. Pliquett, R. Langer, and J. C. Weaver.

"Electrical properties of the epidermal stratum corneum" dated Aug. 12, 1974. By T. Yamamoto and Y. Yamamoto.

"Non-invasive bioimpedance of intact skin: mathematical modeling and experiments" dated May 2, 2010. By U. Birgersson, E. Birgersson, P. Aberg, I. Nicander, and S. Ollmar.

"Polymer Microneedles for Controlled-Release Drug Delivery" dated Dec. 2, 2005. By J-H. Park, M. G. Allen, and M. R. Prausnitz.

"Utilizing Characteristic Electrical Properties of the Epidermal Skin Layers to Detect Fake Fingers in Biometric Fingerprint Systems—A Pilot Study" dated Dec. 1, 2004. By O. G. Martinsen, S. Clausen, J. B. Nysaether, and S. Grimnes.

"Lack of Pain Associated with Microfabricated Microneedles" dated Oct. 10, 2000. By S. Kaushik, A. H. Hord, D. D. Denson, D. V. McAlliser, S. Smitra, M. G. Allen, and M. R. Prausnitz.

"Insertion of microneedles into skin: measurement and prediction of insertion force and needle facture force" dated Dec. 10, 2003. By S. P. Davis, B. J. Landis, Z. H. Adams, M. G. Allen, and M. R. Prausnitz.

"Microneedle Insertion Force Reduction Using Vibratory Actuation" dated 2004. By M. Yang and J. D. Zahn.

"Two Dimensional Metallic Microelectrode Arrays for Extracellular Stimulation and Recording of Neurons" dated 1993. By A. B. Frazier, D. P. O'Brien, and M. G. Allen.

PCT International Search Report of PCT/US2012/065712 dated Mar. 29, 2013 (2 pages).

PCT Written Opinion on the International Searching Authority of PCT/US2012/065712 dated Mar. 29, 2013 (5 pages).

* cited by examiner

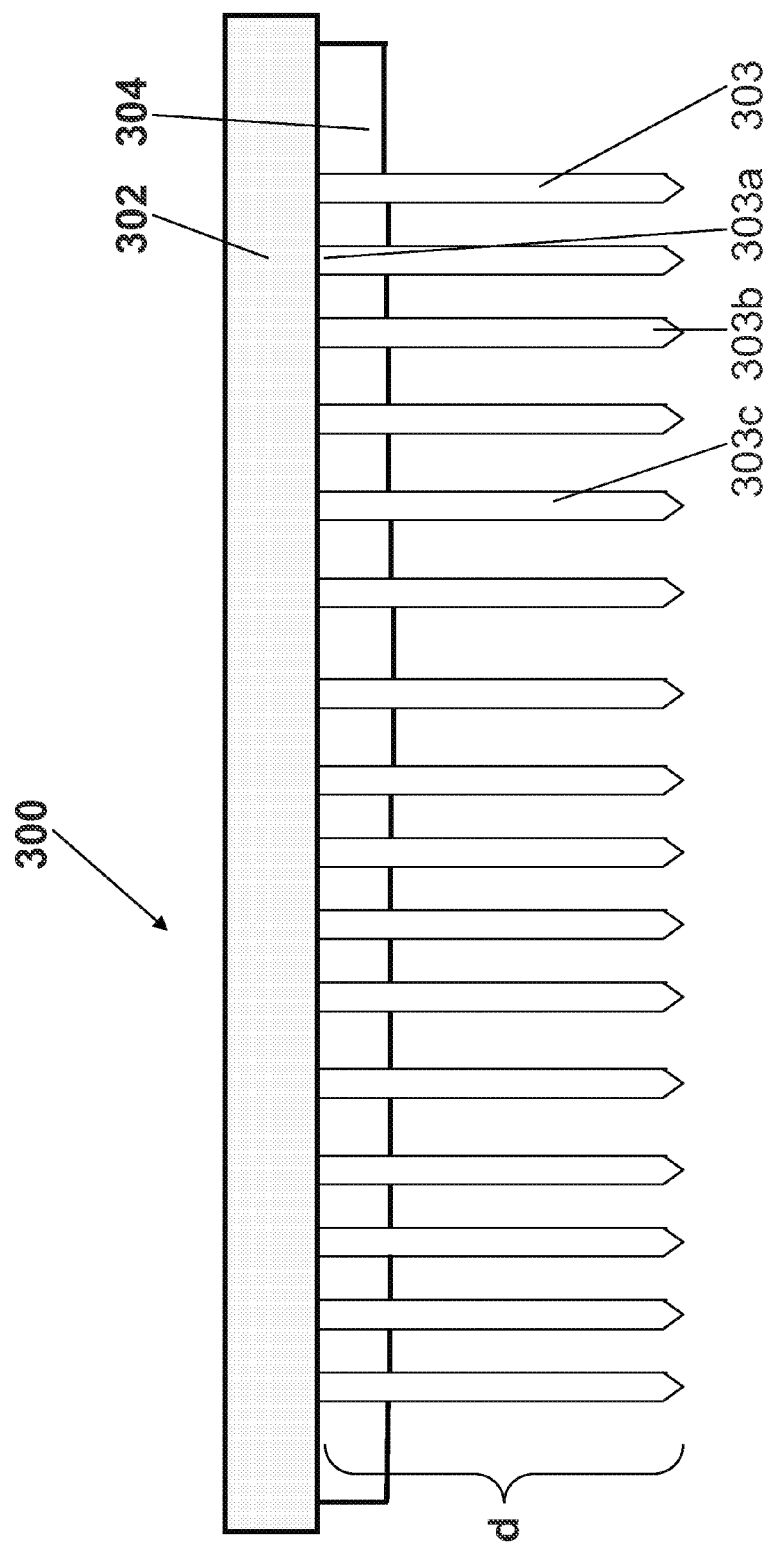

DEVICE AND METHOD FOR REDUCING PATIENT TRANSTHORACIC IMPEDANCE FOR THE PURPOSE OF DELIVERING A THERAPEUTIC CURRENT

PRIORITY CLAIM/RELATED APPLICATIONS

This application is a continuation in part of and claims priority under 35 USC 120 to U.S. patent application Ser. No. 12/724,269 filed on Mar. 15, 2010 now U.S. Pat. No. 8,615,295 and entitled "External Defibrillator" which in turns claims the benefit under 35 USC 119(e) to U.S. Provisional Patent Application Ser. No. 61/161,014 filed on Mar. 17, 2009 and entitled "External Defibrillator", the entirely of both of which are incorporated herein by reference.

FIELD

The disclosure relates generally to a device and method for reducing patient transthoracic impedance for the purpose of delivering a therapeutic current in any animal such as human or non-human animal.

BACKGROUND

A primary task of the heart is to pump oxygenated, nutrient-rich blood throughout the body. Electrical impulses generated by a portion of the heart regulate the pumping cycle. When the electrical impulses follow a regular and consistent pattern, the heart functions normally and the pumping of blood is optimized. When the electrical impulses of the heart are disrupted (i.e., cardiac arrhythmia), sudden cardiac arrest may result, which inhibits the circulation of blood. As a result, the brain and other critical organs are deprived of nutrients and oxygen. A person experiencing sudden cardiac arrest may suddenly lose consciousness and die shortly thereafter if left untreated.

A well known and effective treatment for sudden cardiac arrest or arrhythmia is defibrillation or cardioversion. Defibrillation involves passing a current through the person to shock the heart back into a normal rhythm. There are a wide variety of defibrillators. For example, implantable cardioverter-defibrillators (ICD) involve surgically implanting wire coils and a generator device within a person. ICDs are typically for people at high risk for a cardiac arrhythmia. When a cardiac arrhythmia is detected, a current is automatically passed through the heart of the user with little or no intervention by a third party.

Another, more common type of defibrillator is the automated external defibrillator (AED). Rather than being implanted, the AED is an external device used by a third party to resuscitate a person who has suffered from sudden cardiac arrest. FIG. 1 illustrates a conventional AED 100, which includes a base unit 102 and two pads 104. Sometimes paddles with handles are used instead of the pads 104. The pads 104 are connected to the base unit 102 using electrical cables 106.

A typical protocol for using the AED 100 is as follows. Initially, the person who has suffered from sudden cardiac arrest is placed on the floor. Clothing is removed to reveal the person's chest 108. The pads 104 are applied to appropriate locations on the chest 108, as illustrated in FIG. 1. The electrical system within the base unit 102 generates a high voltage between the two pads 104, which delivers an electrical shock to the person. Ideally, the shock restores a normal cardiac rhythm. In some cases, multiple shocks are required.

Although existing technologies work well, there are continuing efforts to improve the effectiveness, safety and usability of automatic external defibrillators. For example, if the electrical resistance of the patient can be lowered, then it would be possible to have a defibrillator that requires less power, but effectively delivers the therapeutic current to shock the heart.

Currently the main mechanism available to reduce the patient impedance is to increase the size of the electrode pads. The larger the surface area of the electrode pads, then the lower the patient impedance that the defibrillator faces. In addition these electrode pads make use of conductive hydrogel to help ensure that as much of each electrode is in conductive contact with the patient's skin as possible.

Properties of Human Skin

Human skin is the largest organ. Aside from the function of regulating skin temperature, the skin's most important function is to serve as an effective barrier against insult of the body by foreign agents, such as toxic substances, micro-organisms, and due to mechanical injury.

Skin is the outermost protective layer of the body. It is composed of the epidermis, including the stratum corneum, the stratum granulosum, the stratum spinosum, and the stratum basale, and the dermis, containing, among other things, the capillary layer. Below this is the subcutaneous fat layer. Above the skin, and growing outward from within the skin may be found hair, the strands of which can be up to 100 microns in thickness. Some "durable" skin layers such as heels or calluses, can comprise a stratum corneum which is from 100-150 microns thick.

The stratum corneum is a tough, scaly layer made of dead cell tissue. It consists of almost laminated layers of keratin from dead cells. It extends around 10-20 microns from the skin surface and has no blood supply. Because of the density of this layer of cells, moving electrical signals, electromagnetic energy or compounds across the skin, either into or out of the body, can be very difficult. Experiments have found the topmost layers of the stratum corneum to be the most resistant.

The epidermis is typically 50-150 microns in thickness and the dermis, which contains the capillaries and nerve endings is typically 750-1500 microns in thickness. Conductivity of the skin varies by a variety of conditions, such as age, location, sun exposure, use of lotions, moisture level, and ambient conditions, etc.

Removal of the stratum corneum reduces the high impedance of the skin and allows better transmission and reception of electrical signals, electromagnetic energy or biological species into and from human tissues. It has also been demonstrated that electromagnetic energy induced alterations of the stratum corneum result in increased permeability to substances. Alternatively, compounds commonly referred to as "permeation enhancers" can be used, with some success, to penetrate the stratum corneum. Traditional approaches require the abrasion of skin with sand paper and brushes, the stripping of skin with tape and toxic chemicals, the removal of stratum corneum by laser or thermal ablation, or the puncturing of skin with needles.

Thus, it is desirable to provide a better way to reduce patient transthoracic impedance for the purpose of delivering a therapeutic current, such as for a defibrillator or cardioverter, and it is to this end that the disclosure is directed.

BRIEF DESCRIPTION OF THE DRAWINGS

FIGS. 3 and 4 illustrate embodiments of a defibrillator pad with a microneedle array;

DETAILED DESCRIPTION OF ONE OR MORE EMBODIMENTS

The disclosure is particularly applicable to a device and methods for reducing patient transthoracic impedance for the purpose of delivering a therapeutic current in a defibrillator for humans and it is in this context that the disclosure will be described. It will be appreciated, however, that the device and methods for reducing patient transthoracic impedance for the purpose of delivering a therapeutic current has broader applicability to any system in which it is desirable to be able to deliver a therapeutic current and also can be used to deliver a therapeutic current for various purposes and can be used for both humans and animals. To understand the device and methods for reducing patient transthoracic impedance for the purpose of delivering a therapeutic current, an example of a device, a defibrillator, into which the device may be installed, is described.

Figure 1:
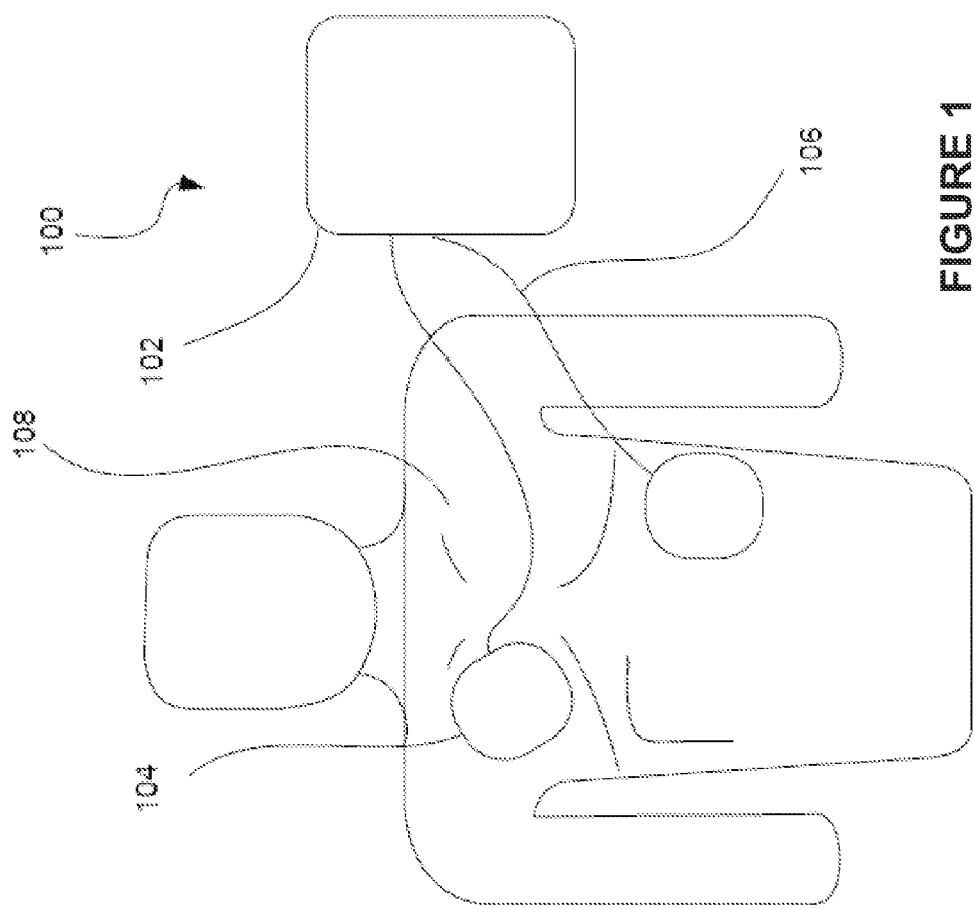
FIG. 1 diagrammatically illustrates an example of a conventional external defibrillator.
Figure 2A:
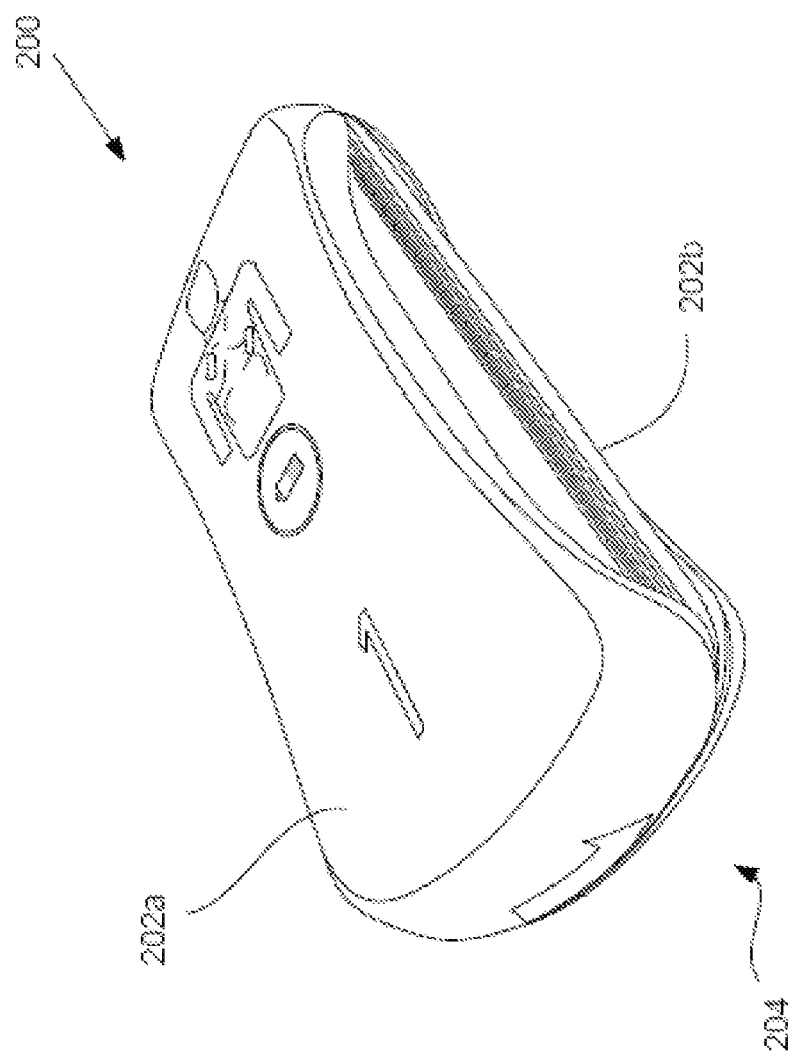
FIGS. 2A and 2B illustrate a perspective view and a side view, respectively, of a external portable defibrillator.
Figure 2B:
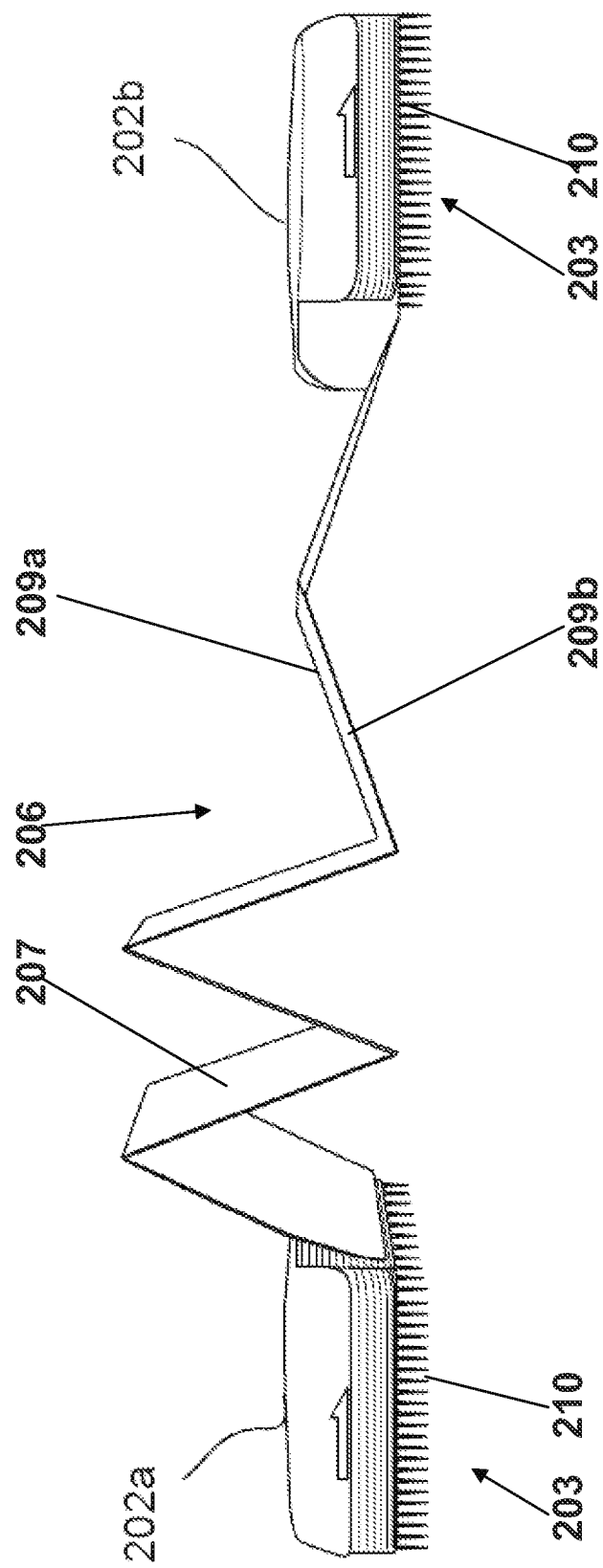
Figure 4:
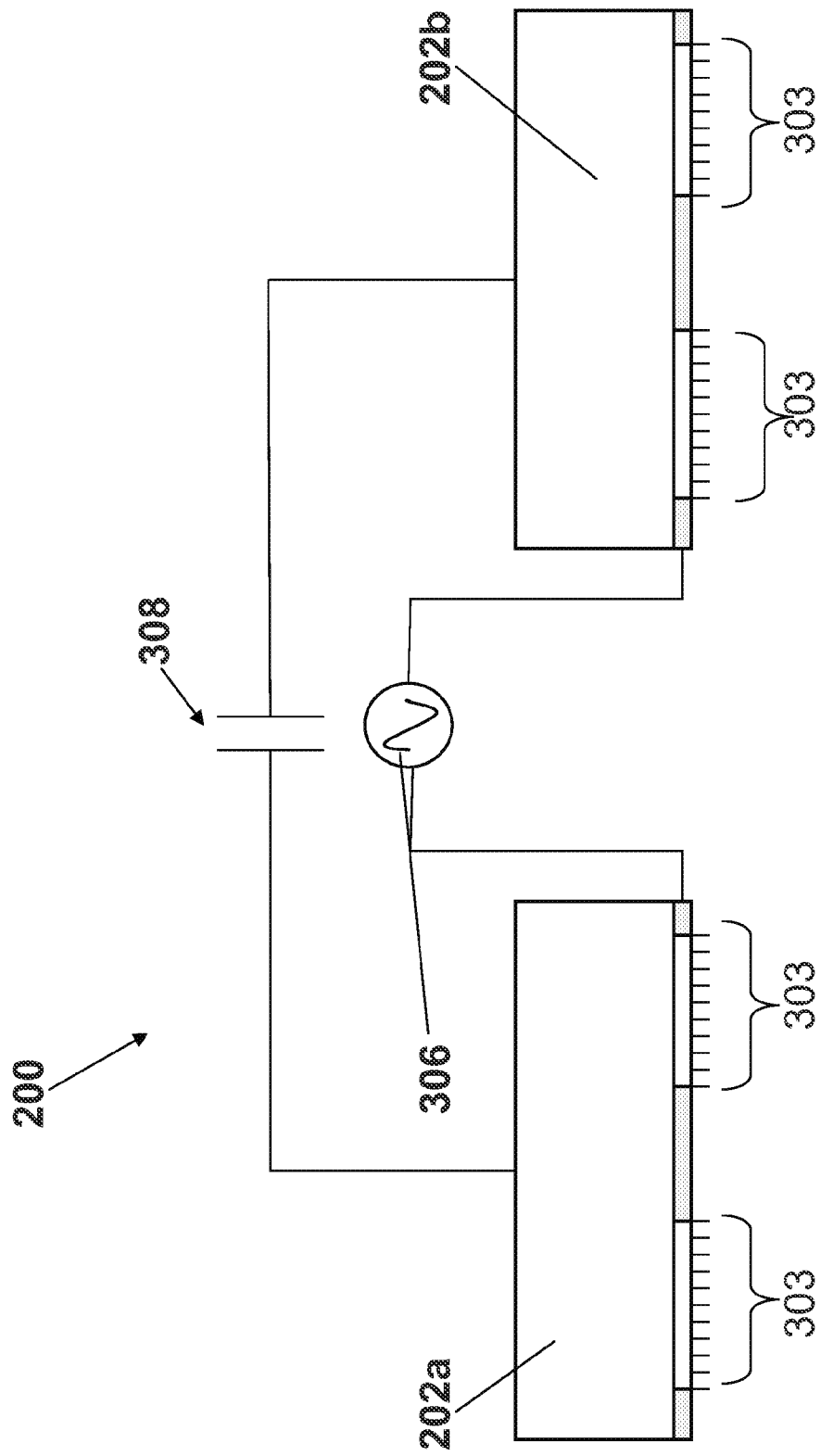

FIGS. 2A and 2B illustrate a perspective view and a side view, respectively, of a external portable defibrillator 200. The defibrillator 200 includes two defibrillator paddles 202a and 202b that are mounted over one another and directly sealed together to form a paddle module 204. When a need arises to defibrillate a victim of sudden cardiac arrest, the paddles 202a and 202b may be pulled apart, which reveals a connecting structure 206, as seen as FIG. 2B, which physically and electrically connects the paddles. The connecting structure 206 may include a sheet-like portion 207 with instructions that help a user operate the defibrillator 200.

Preferably, the paddles 202a and 202b are directly sealed together with a frangible seal. That is, when the paddles 202a and 202b are first pulled apart from one another, the seal is irreversibly and permanently deformed. This feature can have several useful applications. A deformed seal helps indicate whether the paddles 202a and 202b have been used before, which in turn helps indicate whether they are sterile or have sufficient power. Additionally, various events may be triggered by the breaking of the seal. For example, when the seal is broken, one or more capacitors in the defibrillator 200 may start charging without requiring additional input from the user (i.e., a button or other mechanical switch need not be separately triggered to power up the defibrillator.) Upon the opening of the paddle module 204, personal data of the owner of the defibrillator 200 and/or GPS data indicating the location of the defibrillator 200 and/or unique device identification data of the defibrillator 200 may be automatically and wirelessly sent to a remote device or server. As a result, emergency services, medical personnel, family members or other important entities or individuals can be informed automatically and immediately about the use of the defibrillator.

The connecting structure 206 may serve the dual purpose of displaying useful information as well as electrically connecting the paddles 202a and 202b. In some existing AEDs, paddles or patches are individually connected to a base unit with cables. Instructions are typically displayed on the base unit. The base unit and its display, however, take up considerable space in such systems. In the illustrated embodiment, at least some of the instructions are provided on a flexible connecting structure 206 that is compressed between the paddles 202a and 202b when the paddle module 204 is sealed. When the paddle module 204 and the paddles 202a and 202b are pulled apart, the connecting structure 206 unfolds or otherwise decompresses and extends between the paddles 202a and 202b.

The connecting structure 206 is attached to the defibrillator paddles 202a and 202b such that it is easily viewable and can be used as an instructional tool while the user is operating the defibrillator. In the illustrated embodiment, for example, each defibrillator paddle 202a has a defibrillator electrode with an electrically conductive contact surface 203. At the appropriate time, high voltage may be applied at the contact surfaces 203 to deliver an electrical shock. Each sheet-like section 207 of the connecting structure 206 includes a top surface 209a and an opposing bottom surface 209b. The top surface 209a may include images, light emitting devices, light reflecting devices, display screens, electronic display devices, etc. that help instruct the user in the proper operation of the defibrillator. As seen in FIG. 2B, when the defibrillator paddles 202a and 202b are spread out and a conductive contact surfaces 203 of the paddles face downward, instructions on the top surface 209a of the connecting structure 206 tend to face upward. Thus, a user of the defibrillator may easily reference the connecting structure 206 for further instructions and step-by-step guidance while holding the defibrillators over the chest of the victim.

In some embodiments, the portability of the defibrillator 200 may be enhanced by incorporating some or all of the electrical system of the defibrillator into the paddle module 204. While some implementations involve connecting the paddle module 204 via a cable to an external power module, various other approaches involve placing all of the capacitors and batteries of the defibrillator 200 within the housings of the paddles 202a and 202b. Such designs may free the two paddles 202a and 202b from having to connect with a separate third device, which may help make the defibrillator 200 more convenient to carry, access and operate.

Generally, the overall volume of the defibrillator 200 is influenced by the capacity of its electrical system. A defibrillator that is capable of delivering more shocks and charging the capacitors more times generally has more and/or larger batteries. More specifically, a larger battery can typically support a greater number of electrical shocks than a smaller one before requiring replacement or recharging. As far as the inventors are aware, existing AEDs have the capacity to deliver many shocks e.g., at least 50 shocks or many more than are typically needed to treat a single cardiac arrest victim.

As shown in FIG. 2B, each paddle has a set of conductive protrusions 210 that extend out of each defibrillator paddle 202*a* and 202*b*. The conductive protrusions 210 are coupled with the electrical system of the defibrillator 200. The electrical system, which includes one or more batteries and capacitors, may be stored within one or more of the defibrillator paddles 202*a* and 202*b*, as shown in FIG. 2A, or in an external power module. The conductive protrusions 210 are part of the defibrillator electrode in each paddle and are arranged to optimize current flow through a sudden cardiac arrest victim.

Generally, the conductive protrusions 210 are arranged to press or penetrate into the skin of the victim. Such pressing or penetration reduces the electrical resistance of the skin (e.g., reduces the patient transthoracic impedance for the purpose of delivering a therapeutic current.) As a result, less voltage needs to be generated at the conductive protrusions 210 to ensure a current sufficient to arrest a cardiac arrhythmia in the victim. The corresponding reduction in power requirements for the defibrillator 200 may translate into a reduction in size of the electrical system of the defibrillator (e.g., a reduction in the size of its capacitors and/or batteries), which in turn helps enhance the portability of the defibrillator 200. In some embodiments, the volume of all capacitors in the defibrillator 200 may be limited to a total volume of approximately 400 cubic centimeters or less. In still other embodiments, the defibrillator 200 is arranged to apply a voltage at the defibrillator electrodes that is never in excess of 1400 volts during the normal operation of the defibrillator. (In comparison, some existing AEDs require the application of much more than 1400 volts to defibrillate a person.) The conductive protrusions 210 may be, in one embodiment that is described below, a microneedle array.

The defibrillator may also use other methods such as electroporation and/or sonophoresis to reduce patient transthoracic impedance for the purpose of delivering a therapeutic current. The electroporation and/or sonophoresis characteristics (as described below) are assessed electronically prior to energy delivery to the subject and those characteristics and how they are assessed are well known in the art.

Electroportation

The movement of substances, electrical signals or electromagnetic energy transdermally or intradermally may also be aided by a process of electroporation. Electroporation is typically carried out by high voltage pulses applied to a pair of electrodes, which are applied to a tissue surface. The electric pulses cause the passing ions to perforate the tissue layer, providing new pathways for the passage of substances, both charged and not charged. It must be noted that electroporation does not deliver a charged substance, but rather reduces the resistance to passage of substances into the adjacent tissue. Because it does not provide a needed driving force, it is desirable that electroporation be combined with delivery techniques such as iontophoresis or electrophoresis in order to achieve good penetration.

It is known that the main impediment in the passage of electrical current through the skin is attributed to the dead keratin layers of the stratum corneum (SC). These layers, which are relatively dry, possess low electrical conductivity and consequently inhibits the electromotive forces of the iontophoretic device. As illustrated in all textbooks, because of the high impedance of the stratum corneum, electrical current has to pass through the deeper layers of the skin, i.e. the lower epidermis and the dermis, thereby, carrying active agents into the deep layers and subsequently, into the systemic circulation. Thus, it is understood that improving SC conductivity should result in more electrical current passing through the SC and consequently, higher delivery of the active electrical impulse to the target organ, in this case, the myocardium, rather than being attenuated through the external layers of the skin.

Electroporation, or electropermeabilization, is the phenomenon in which cell membrane permeability to ions and macromolecules is increased by exposing the cell to short (microsecond to millisecond) high voltage electric field pulses (See, for example, E. Neumann, M. Schaeffer-Ridder, Y. Wang, P. H. Hofschneider, Gene transfer into mouse lymphoma cells by electroporation in high electric fields, EMBO J 1 (1982) 841-845.). Experiments show that the application of electrical pulses can have several different effects on the cell membrane, as a function of various pulse parameters; such as amplitude, length, shape, number of repeats and intervals between pulses. As a function of these parameters, the application of the electrical pulse can have no effect, can have a transient permeabilization effect known as reversible electroporation or can cause permanent permeabilization known as irreversible electroporation. Both, reversible and irreversible electroporation have important application in biotechnology and medicine.

When electroporation is used to force a current flow across different tissue layers, those with tissue layers with the higher resistivity will be subjected to higher electric fields. Thus, some tissue layers will be more prone to electroporation than others. Since it is possible to reversibly electroporate some tissues while irreversible electroporate others tissues (or burn the tissues) because of a Joule effect, it will be difficult to assess the required external voltage in order to have the sufficient electric field at the region of interest.

A controlled electroporation system, in order to induce temporary reversible electroporation of the stratum corneum whereby the pores become enlarged and remain open for an extended duration, the system may use high voltage pulses (over 100V) of high frequency over a short duration. An example is 8 pulses of 750V, each of a duration of 100 microseconds over a total period of 1 second. Typically pulses have an amplitude of about 10 to 200 kV/cm and a pulse length of one or several hundreds of picoseconds to one or several tens or hundreds of nanoseconds.

During a simulating pulse that causes electroporation, a large voltage exists across the biological barrier (the cell membrane in the first case; the approximately 100 micron lipid bilayer membranes of the SC in the case of the skin), and a greatly diminished electrical resistance occurs across that barrier. In many instances, the resistance returns to prepulse values, or nearly prepulse values, comprising "reversible electroporation." For the larger pulses, and for longer pulses, artificial planar bilayer membranes exhibit irreversible breakdown, and are destroyed so that resistance across the site of the membrane remains at a greatly diminished value. Similarly, for the larger pulses, and for longer pulses, cell membranes remain in an open state, with a greatly diminished transmembrane resistance, and the cell is usually killed. In the case of skin, for the larger pulses, and for longer pulses, $R_{skin}$ can remain at values much smaller than the initial, prepulse values. This lack of recovery is often viewed as evidence of damage to electroporated cells, often fatal damage, in the case of the SC lack of recovery is often assumed to be undesirable, even though the SC is a dead tissue. Further, a lack of recovery means that the adjacent, viable epidermis is exposed through the persistent pathways to the external environment, i.e. some of the protective feature of the skin has been lost. Thus, against the background of artificial planar bilayer membrane electroporation and cell membrane electroporation, the use of large and/or long pulses that cause skin electroporation but with slight or essentially no recovery of $R_{skin}$ is viewed as undesirable.

For a controlled sonophoresis system, ultrasound at a frequency such as 55 kHz is applied to the patients' skin for 5 to 30 seconds using a suitable device such as the Sontra SonoPrep® ultrasonic skin permeation device. The ultrasound is applied until the conductivity feedback threshold is attained.

MicroNeedles

The defibrillator may also use microneedles since very little (if any) pain, local damage, bleeding, or risk of infection is caused by microneedles. The research has demonstrated that microprobes with cross-sections on the order of tens of micrometers can penetrate living tissue without causing significant trauma. The term "trauma" is defined herein as "pain associated with the application of the article of manufacture to the surface of skin, bleeding, bruising, swelling, damage to skin areas, and the like."

As shown in FIG. 3, a microneedle structure 300 may include a substrate 302 having an exterior surface. The microneedle structure 300 may include a plurality of microneedles 303 attached to the substrate 302 and projecting outwardly a distance, d, from the exterior side of the substrate. For example, each microneedle may have a length (equal to d) that ranges from 50 microns to 300 microns and may also have an outer diameter range of 10 microns to 250 microns. Each microneedle 303 includes a proximate end 303a, a distal end 303b and an outer surface 303c. In a defibrillator, the microneedle structure may also have a lower substrate 304 that is gel-like for ECG sensing and to ensure the maximum surface area contact. In the defibrillator, the two paddles 202a, 202b have the microneedles 303 as well as well known ECG sensing circuit 306 and a defibrillator shock circuit 308 from the capacitor.

The system includes an active electrode assembly, a counter electrode assembly, both of which incorporate a multitude of functionalized microneedles. The conductive microneedle arrays are added to the patient facing surface of the electrode pads and are in electrical contact with the device's capacitor, battery and control electronics. The microneedles effectively increase the surface area of the modified electrode pads. The electrode pads now have a 3 dimensional surface area that is significantly larger than the purely two dimensional surface that they previously had. This decreases the current density in the patient's skin and flesh and reduces the likelihood of any tissue damage from the high voltage and current in the defibrillation pulse. This increase in surface area can be further influenced through the use of microneedles with an increased tip area geometry, such as the ZP-Titanium microneedle arrays available from Zosano Pharma. This increases the surface area of the electrode that is directly in contact with the conductive tissues of the deeper epidermis.

Figure 5:
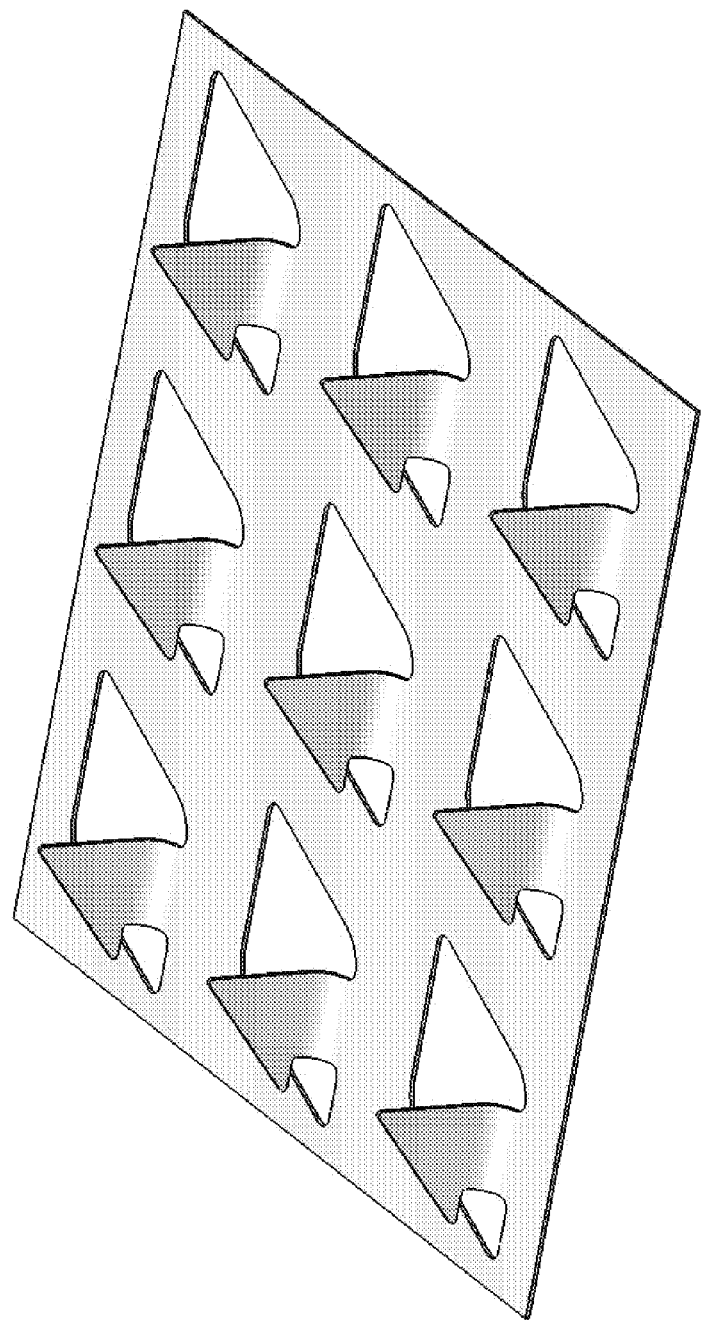
FIG. 5 illustrates an embodiment of a microneedle array.
Figure 6:
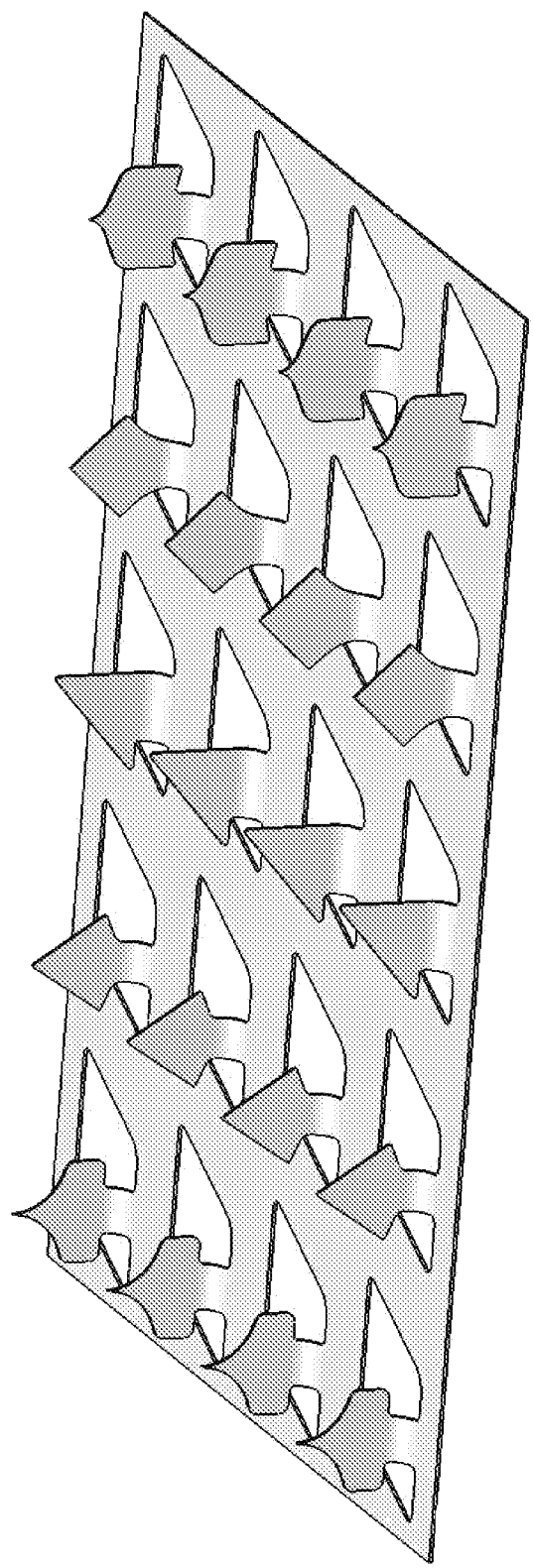
FIG. 6 illustrates another embodiment of a microneedle array.
Figure 7:
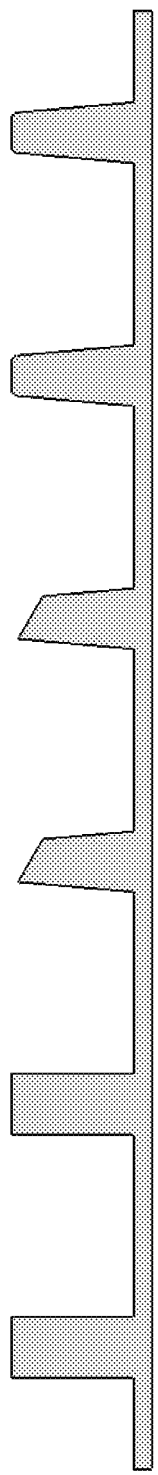
FIG. 7 illustrates another embodiment of a microneedle array with solid microneedles.
Figure 8:
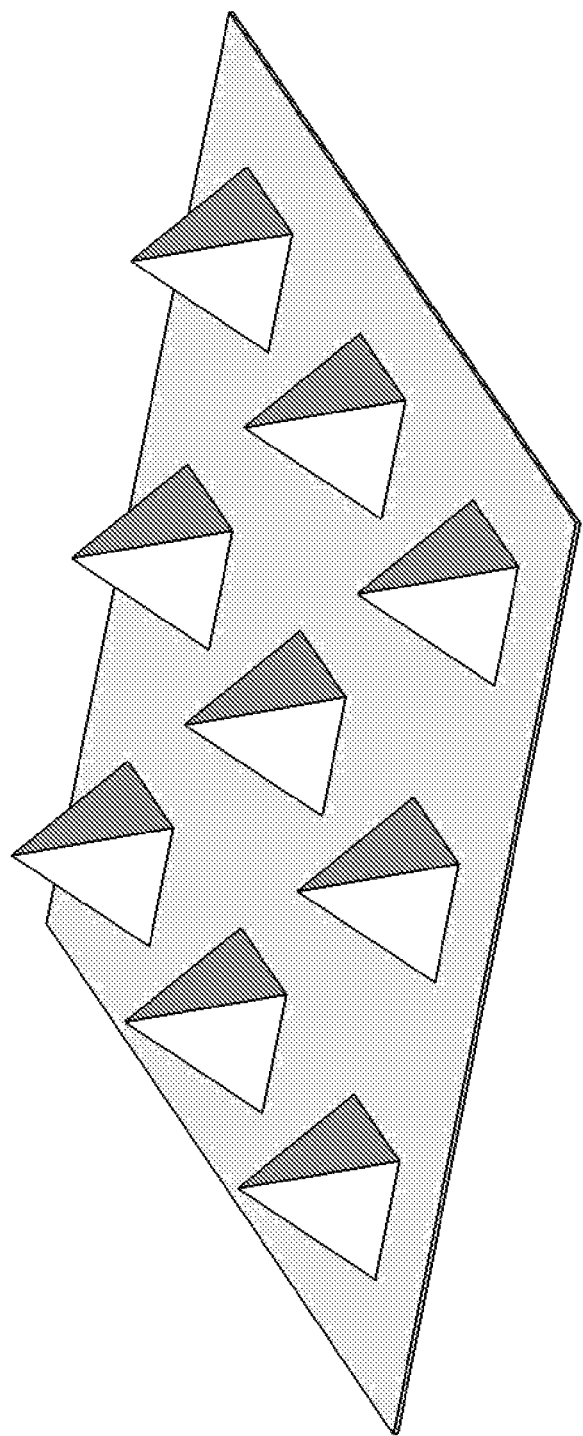
FIG. 8 illustrates another embodiment of a microneedle array with solid pyramid shaped microneedles.
Figure 9:
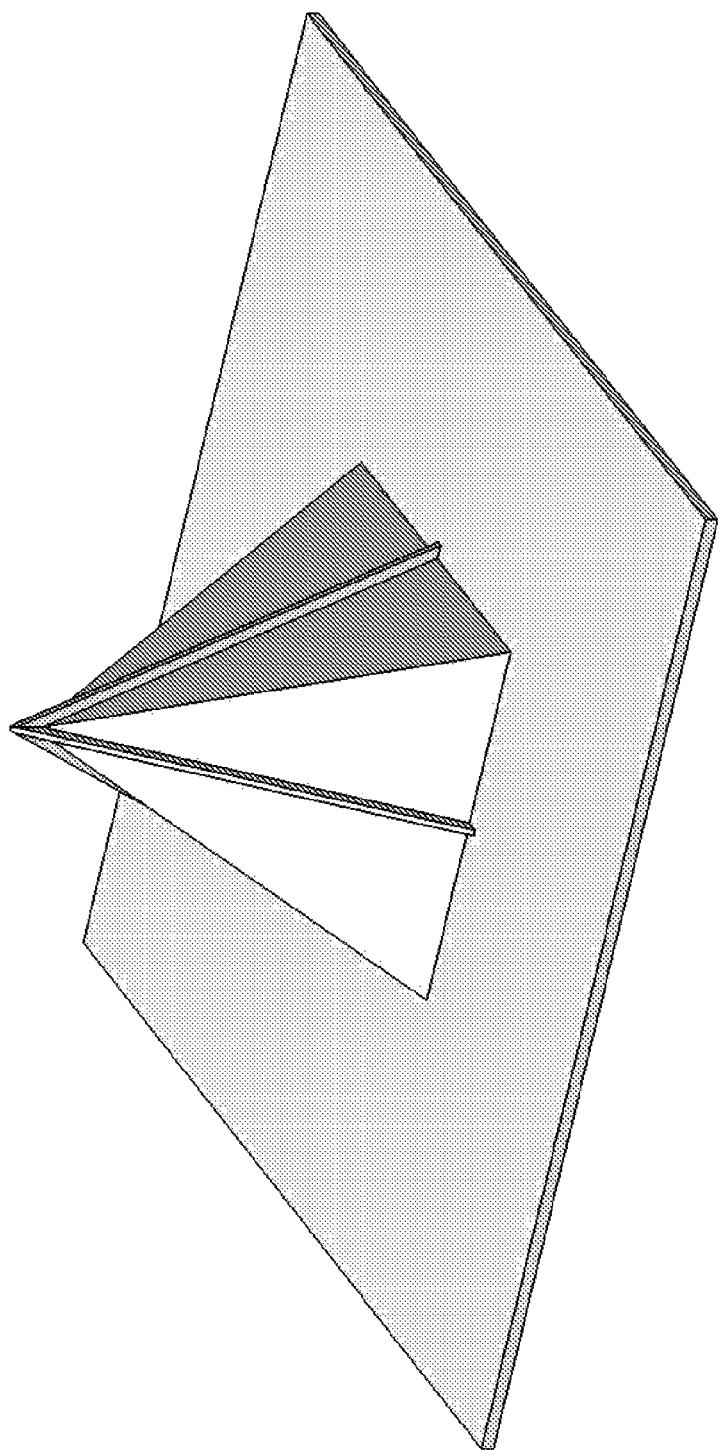
FIG. 9 illustrates another embodiment of a microneedle array with solid pyramid shaped microneedles.
Figure 10:
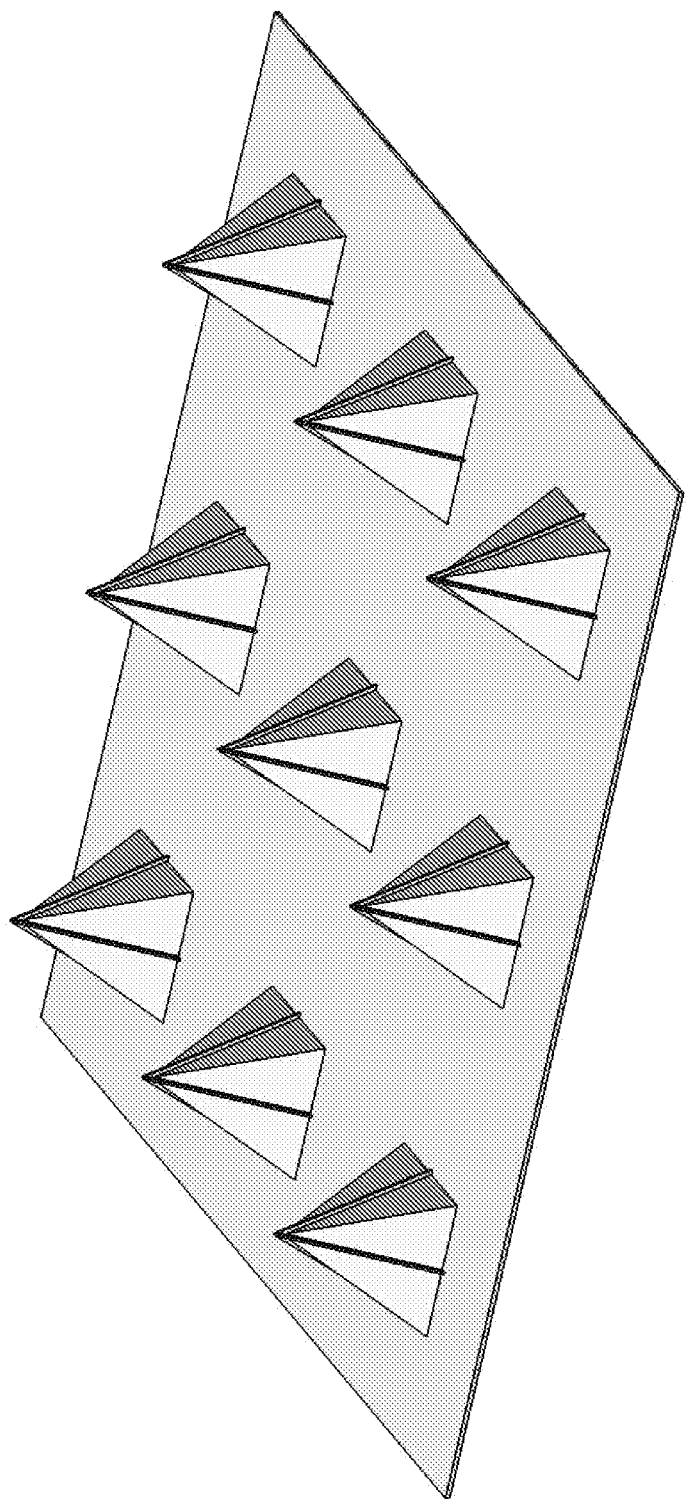
FIG. 10 illustrates another embodiment of a microneedle array with solid pyramid shaped microneedles.
Figure 11:
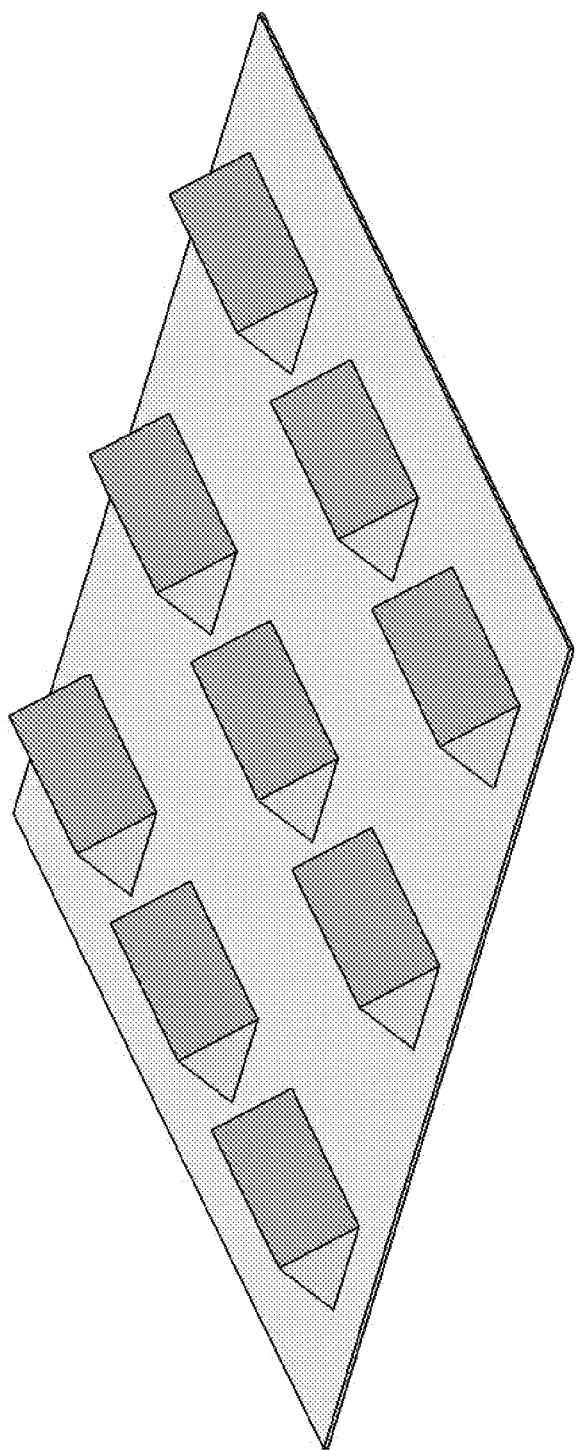
FIG. 11 illustrates another embodiment of a microneedle array with prism microneedles.
Figure 12:
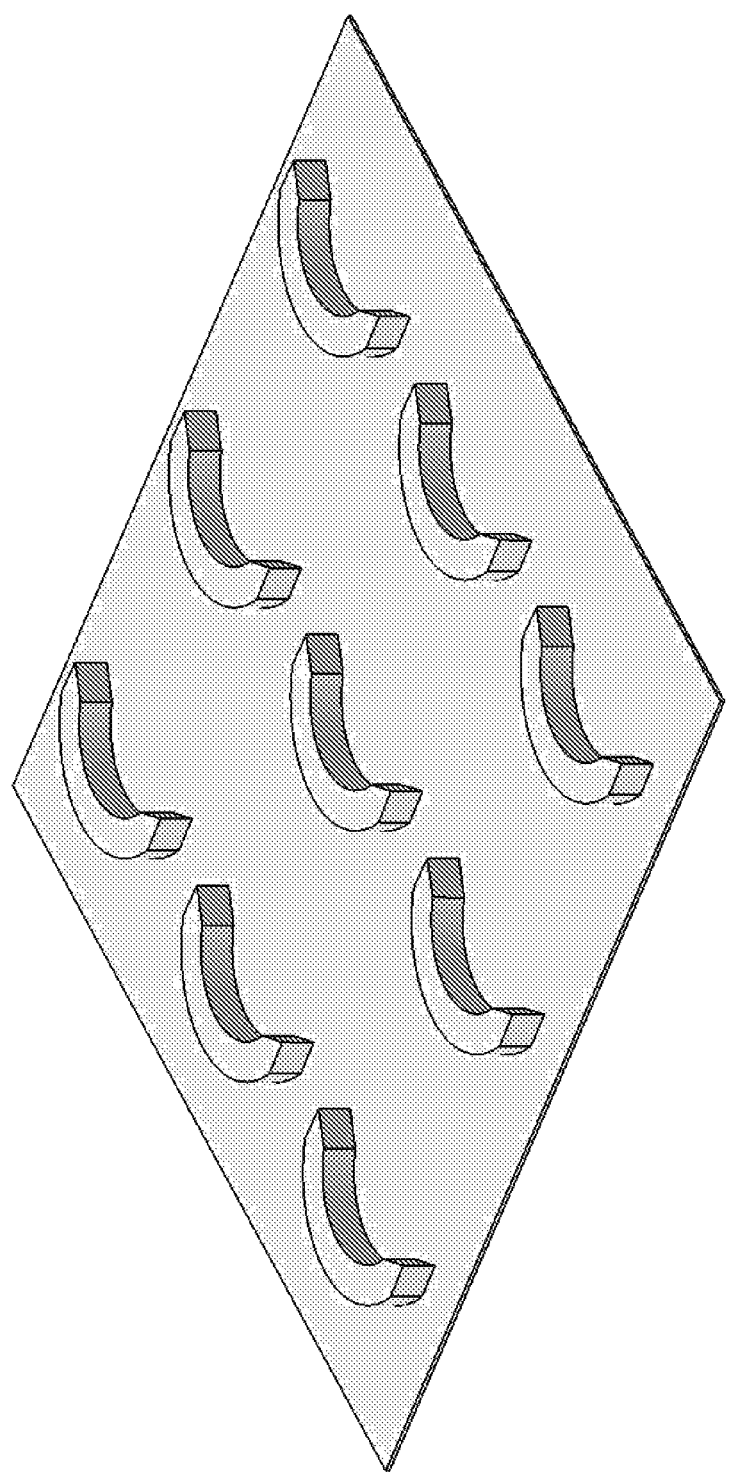
FIG. 12 illustrates another embodiment of a microneedle array with curved blade microneedles.
Figure 13:
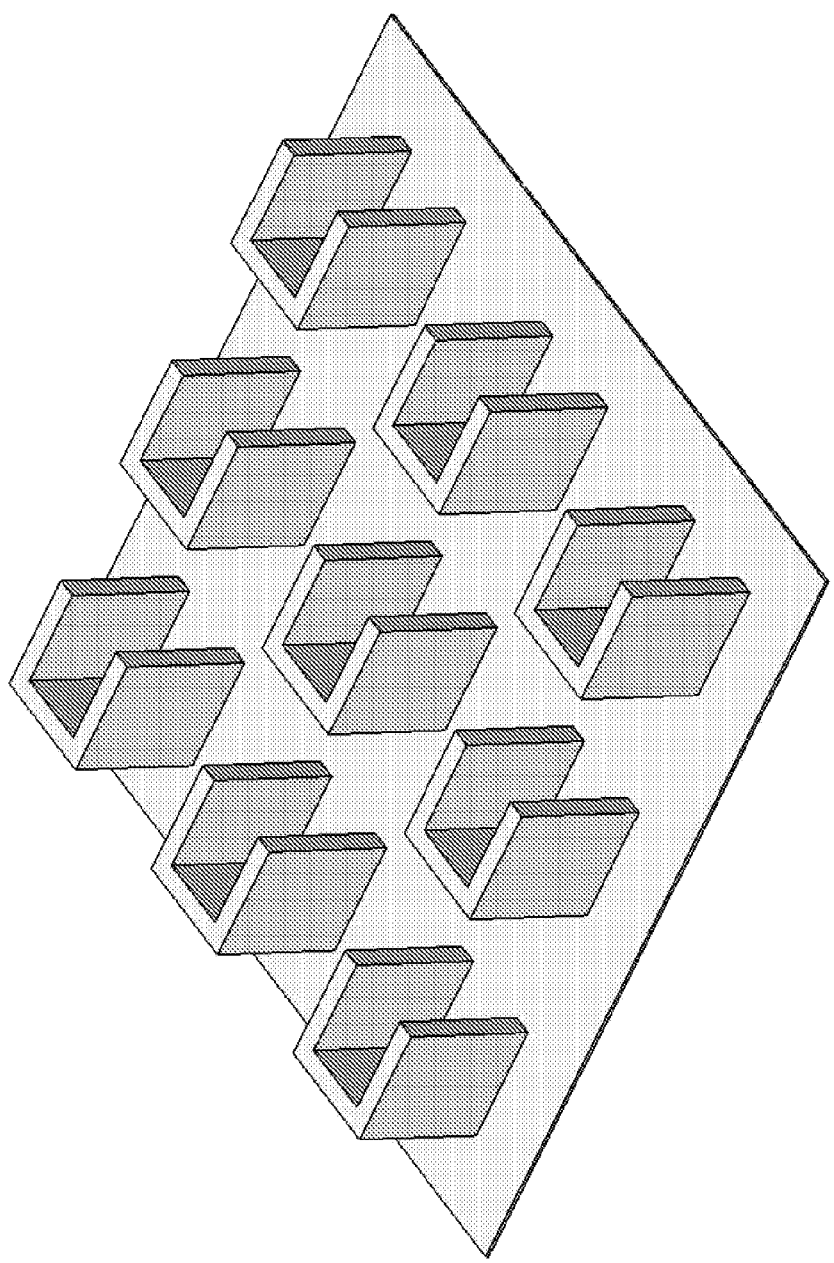
FIG. 13 illustrates another embodiment of a microneedle array with C-channel microneedles.

The microneedles may or may not be integrally formed from the substrate although they are shown integrally formed with the substrate in FIG. 3. The microneedles may take a variety of shapes and forms. For example, the distal end of the microneedle may be sharp or dull, and may take a beveled, parabolic, flat-tipped, sharp-tip, blunt-tipped, radius-tipped, chisel-like, tapered and/or tapered-cone-like form. Furthermore, the outer shape of the microneedles, including the outer surface may take any form including a right cylinder, and oblique cylinder, a circular cylinder, a polygonal cylinder, or any other tapered, regular or irregular shape. Preferably, the microneedles are provided as a multi-dimensional array, in contrast to a device with a single microneedle or a single row of microneedles. The microneedle device can be adapted to be a single-use disposable device, or can be adapted to be fully or partially reusable. The array of microneedles can include a mixture of microneedle orientations, heights, or other parameters. Examples of different microneedles are shown in FIGS. 5-13. FIG. 5 shows an array of microneedles cut from a conductive sheet in which each microneedle has the same shape whereas FIG. 6 shows an array of microneedles cut from a conductive sheet in which each microneedle has a slightly different shape. In this embodiment, the larger surface area of the conductive microneedle that penetrates the skin then the larger the effective surface area of the electrode is which allows the effective patient impedance to be reduced and hence reduces the total amount of energy that needs to be delivered, or else the physical size of the electrode can be reduced. FIGS. 7-13 illustrate different examples of solid microneedles (since the microneedles can be solid or hollow), such as a cylindrical solid microneedle in FIG. 7, a pyramidal solid microneedle in FIG. 8, a solid pyramidal microneedle with an extended portion to increase the surface area in FIG. 9 and an array in FIG. 10, a solid prism shaped microneedle array in FIG. 11, a solid curved blade microneedle array in FIG. 12 and a C-channel shaped microneedle array in FIG. 13.

The microneedles are made by known microfabrication processes by creating small mechanical structures in silicon, metal, polymer, and other materials. These microfabrication processes are based on well-established methods used to make integrated circuits, electronic packages and other microelectronic devices, augmented by additional methods used in the field of micromachining. The microneedle devices can have dimensions as small as a few nanometers and can be mass-produced at low per-unit costs. Microfabrication processes that may be used in making the microneedles disclosed herein include lithography; etching techniques, such as wet chemical, dry, and photoresist removal; thermal oxidation of silicon; electroplating and electrode-less plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation).

The conductive microneedles (since they need to be able to conduct current) are made from the following range of conductive materials that includes, but is not limited to: metals, ceramics, semiconductors, organics, polymers, and composites. The preferred materials include pharmaceutical grade stainless steel, gold, titanium, nickel, iron, gold, platinum, tin, chromium, copper, alloys of these or other metals, silicon, silicon dioxide, capacitive carbon, graphite and polymers. Ideally the embodiment uses biocompatible materials such as a nickel titanium alloy, titanium, or stainless steel. One embodiment includes microneedles made of metal, such as titanium or stainless steel. Metal microneedles are advantageous because they are durable, semi-flexible, and have the mechanical strength to endure insertion into the stratum corneum, can be cut from readily available, relatively inexpensive commercial stock via a chemical saw, or any suitable technique, to the desired dimensions, and ground to the desired tip geometry.

In addition to the exemplary microneedles described above, the microneedles can be formed with shafts that have a circular cross-section in the perpendicular, or the cross-section can be non-circular. For example, the cross-section of the microneedle can be polygonal (e.g. star-shaped, square, triangular, circular), oblong, or another symmetrical or asymmetrical shape or even faceted structures including prismatoids, conicals, polyhedrons, pyramids, prisms, wedges and the like. The shaft can have one or more bores. The cross-sectional dimensions typically are between about 10 nm and 1 mm, preferably between 1 micron and 200 microns, and more preferably between 10 and 100 µm. The outer diameter is typically between about 10 microns and about 100 microns.

For circular solid microneedles, a useful outer diameter range is from 10-100 microns, and more preferably in the range of 20-50 microns. For circular microneedles that do not have sharp edges, a useful length for use is in the range of 50-1200 microns, and more preferably in the range of 100-400 microns. For circular microneedles having sharp side edges, a useful length for use is in the range of 50-1200 microns, and more preferably in the range of 80-400 microns.

For solid microneedles having a star-shaped profile with sharp edges for its star-shaped blades, a useful length for use is in the range of 50-1200 microns, and more preferably in the range of 80-400 microns; while the radius of each of its blades is in the range of 10-50 microns, and more preferably in the range of 10-15 microns.

Other preferred embodiments include methods of maximizing the surface area of the microneedles that are embedded into the skin, such as surface protrusions from the flat sides of a pyramidal shaped microneedle.

The microneedles, such as those shown in FIGS. 5-6, may be pressed or etched out of a sheet of material and then deformed into microprotusions that are at a 90 degree angle from the plane of the sheet. Examples of these microneedles are the ones manufactured by Zosano Pharma and Nano BioSciences.

In most embodiments, the microneedles can be oriented perpendicular or at another angle to the substrate. Preferably, the microneedles are oriented perpendicular to the substrate so that a larger density of microneedles per unit area of substrate is provided. However, an array of microneedles can include a mixture of microneedle orientations, heights, or other parameters.

The microneedle arrays may also have a particular needle density (a number of needle within a particular area.) For example, a useful range of separation distances between microneedles is in the range of 100-1400 microns, and more preferably in the range of 100-400 microns. The outer diameter and microneedle length is also very important, and in combination with the separation distance will be crucial as to whether or not the microneedles will actually penetrate the stratum corneum of skin. In one embodiment, the microneedle array has a microneedle density of at least approximately 10 microneedles/cm$^2$, more preferably, in the range of at least approximately 200-2000 microneedles/cm$_2$.

Maximizing Skin Contact

The microneedle arrays may be used in conjunction with a conductive hydrogel to ensure maximized surface area of contact. Various electrically conductive hydrogels have been known used in the medical field to provide an electrical interface to the skin of a subject or within a device to couple electrical stimulus into the subject. Hydrogels hydrate the skin, thus protecting against burning due to electrical stimulation through the hydrogel, while swelling the skin and allowing more efficient transfer of electrical current or signal.

Examples of hydrogels are disclosed in U.S. Pat. Nos. 6,803,420; 6,576,712; 6,908,681; 6,596,401; 6,329,488; 6,197,324; 5,290,585; 6,797,276; 5,800,685; 5,660,178; 5,573,668; 5,536,768; 5,489,624; 5,362,420; 5,338,490; and 5,240,995 herein incorporated in their entirety by reference. Further examples of such hydrogels are disclosed in U.S. Patent applications 2004/166147; 2004/105834; and 2004/247655, herein incorporated in their entirety by reference. Product brand names of various hydrogels and hydrogel sheets include Corplex™ by Corium, Tegagel™ by 3M, PuraMatrix™ by BD, Vigilon™ by Bard, Clearsite™ by Conmed Corporation, FlexiGel™ by Smith & Nephew, Derma-Gel™ by Medline, Nu-Gel™ by Johnson & Johnson, and Curagel™ by Kendall, or acrylhydrogel films available from Sun Contact Lens Co., Ltd.

In one embodiment of the device, the substrate, as well as other components, are formed from flexible materials to allow the device to fit the contours of the biological barrier, such as the skin to which the device is applied. A flexible device may facilitate more consistent penetration of some biological barriers, because penetration can be limited by deviations in the attachment surface. For example, the surface of human skin is not flat due to dermatoglyphics (i.e. tiny wrinkles) and hair. However, for some biological barriers, a rigid substrate may be preferred.

In another embodiment to adapt to the deformability of skin, the microneedle device includes arrays of microneedles having spaces between the microneedles or between arrays of microneedles, wherein the spacing permit areas of the skin to fill the spaces in order to enhance microneedle contact with adjacent areas of the skin. The spacing is designed to adapt to the skin's radius of curvature to overcome the penetration problem.

In a preferred embodiment, the microneedle device includes an adhesive material to secure the microneedle device to the skin, temporarily immobilizing the microneedles while inserted into the skin to deliver the current. The adhesive agent typically is applied to the substrate (in between the microneedles at their base) or to an attachment collar or tabs adjacent the microneedles.

The defibrillator may have an impedance sensor having an electrode positioned to measure the impedance of a portion of the target area between the needle and the electrode, the impedance being indicative of the depth of penetration of the needle into the target area. The impedance sensor which measures the impedance of a portion of the target area between two of the at least two needles when the two needles have penetrated into the target area, the impedance being indicative of the depth of penetration of the needles into the target area. In some embodiments, the measured impedance after the needle penetrates the skin is an order of magnitude less than the measured impedance before the needle penetrates the skin, and, in particular embodiments, the impedance drops by over three orders of magnitude when the needle has penetrated to the proper depth.

As stratum corneum depth varies, the applicator uses the impedance sensor to determine when the stratum corneum has been transverse. The impedance sensor measures impedance of electric current flow between two of the microneedles. Impedance is high in the stratum corneum, and drops dramatically in the portion of the dermis just below the stratum corneum. The sensor reads the change in impedance as the microneedles penetrate into the skin, and movement is stopped when the impedance drops by an order of magnitude. Additionally or alternatively, there can be a hard mechanical stop, for example, the top of the ports, that prevents the microneedles from penetrating too deeply. The impedance sensors are well known in the art.

The device packaging of the defibrillator should prevent contamination and damage to the microneedles during manufacturing, packaging, storage, shipment and sale before use. It is particularly important that the microneedle device is provided with a removable protective cover or cushion that protects the microneedles from damage. In one embodiment, an adhesive material or gel film used to selectively secure the cover over the microneedles may be used. In an alternate embodiment, the film is antiseptic, and following removal can serve as a wipe or adhesive strip to prepare the skin surface before insertion of the microneedles.

Figure 14:
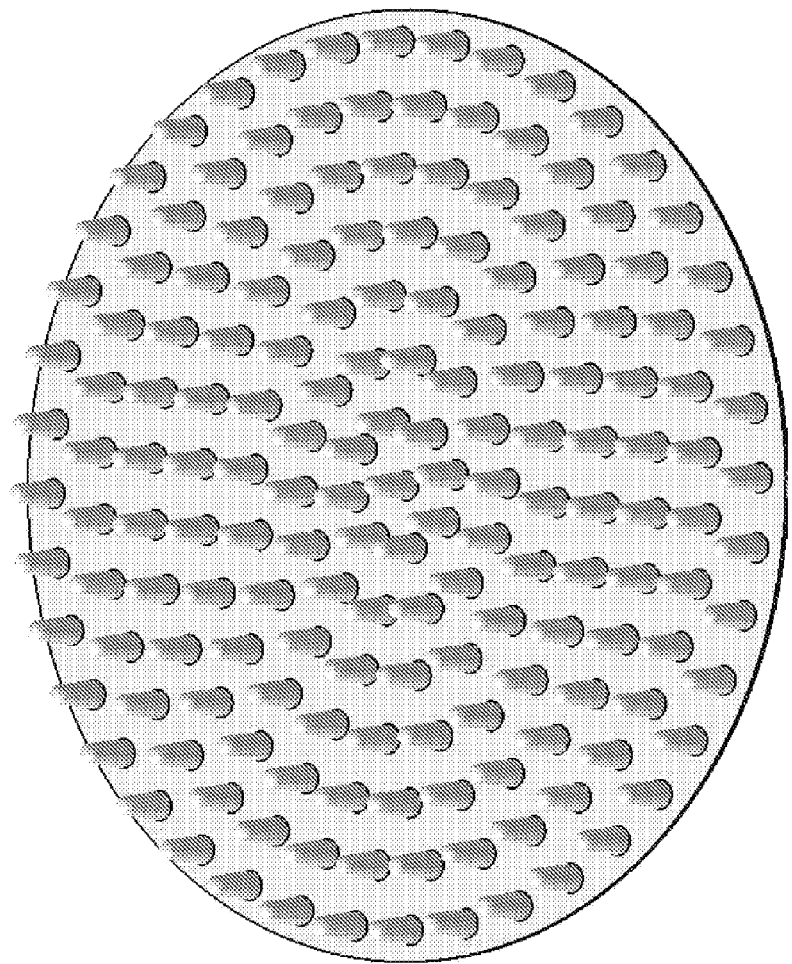
FIG. 14 illustrates an example of a defibrillator electrode pad/paddle with the patient-facing surface covered by a microneedle array.
Figure 15:
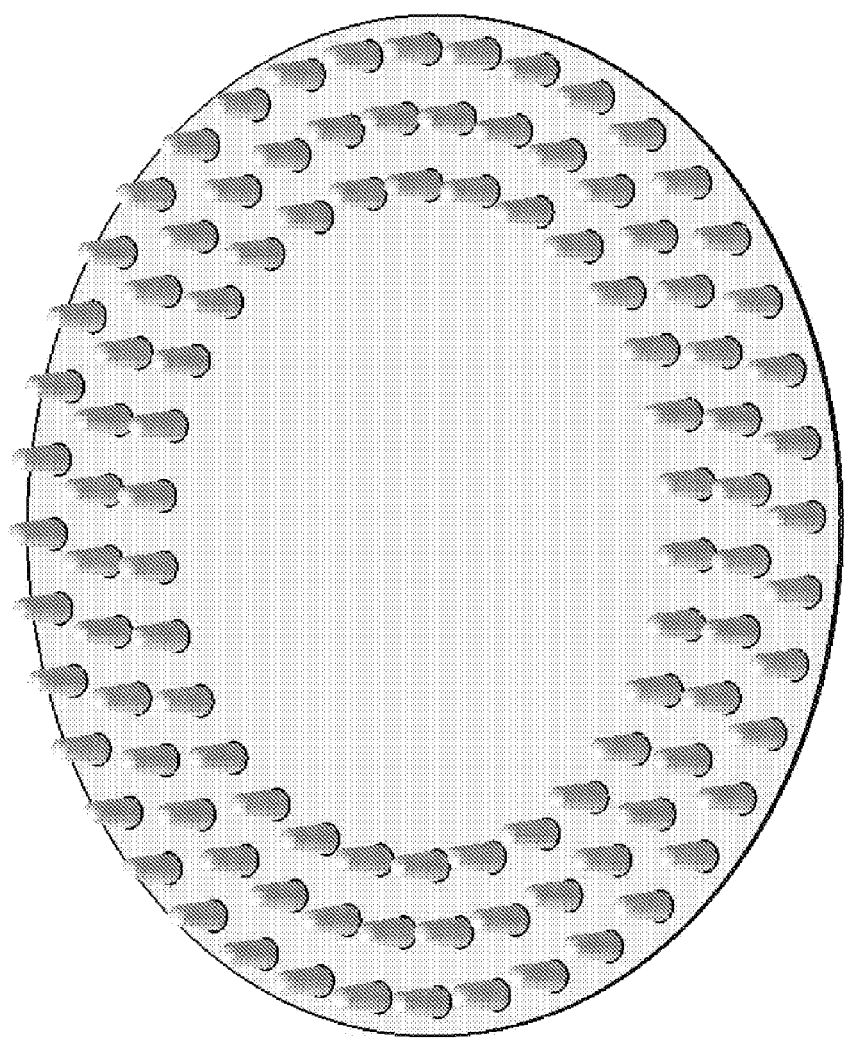
FIG. 15 illustrates an example of a defibrillator electrode pad/paddle with an outer circumference of its patient-facing surface covered by a microneedle array and the center without microneedles where electroconductive gel is used to sense the ECG signals from the patient.
Figure 16:
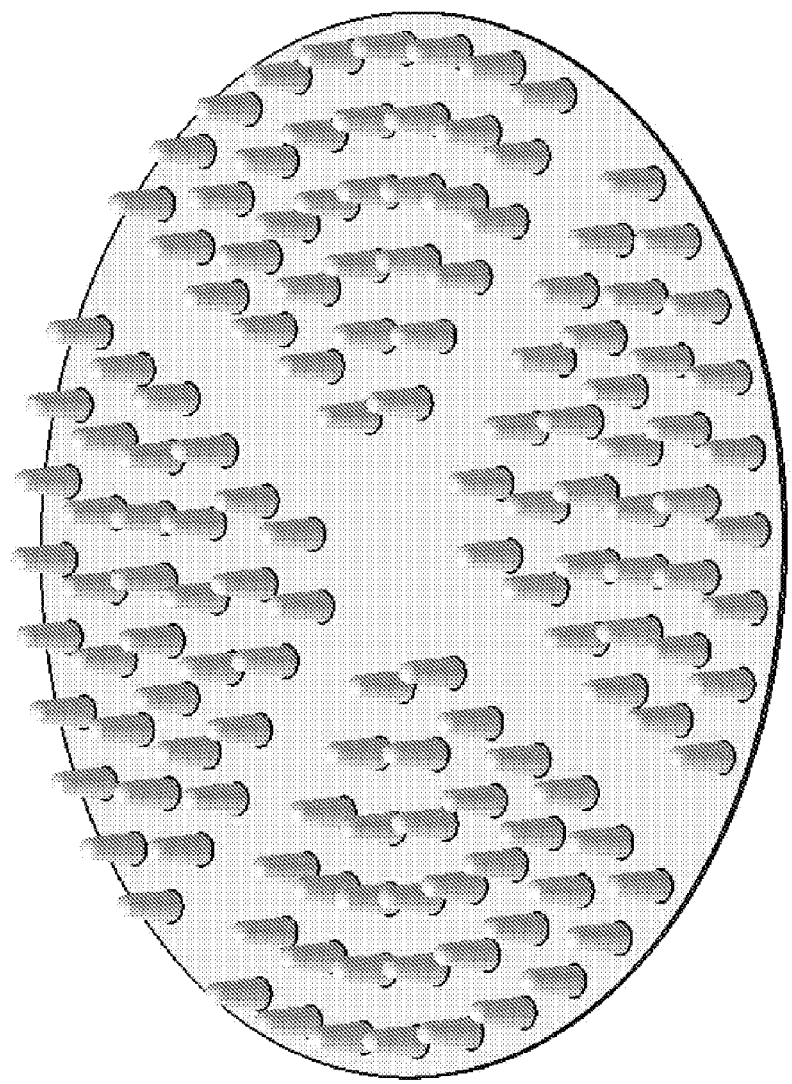
FIG. 16 illustrates an example of a defibrillator electrode pad/paddle with a majority of the patient-facing surface covered by a microneedle array and the central channels without microneedles where electroconductive gel is used to sense the ECG signals from the patient.
Figure 17:
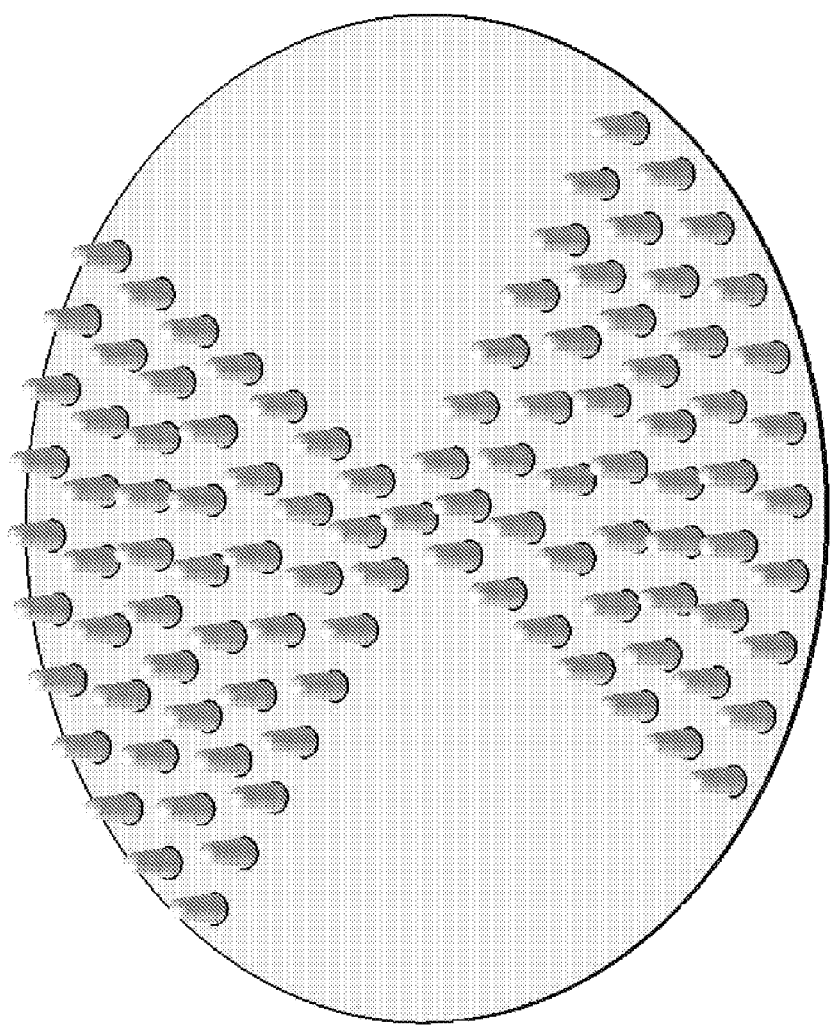
FIG. 17 illustrates an example of a defibrillator electrode pad/paddle with the patient-facing surface covered by a microneedle array and regions without microneedles where electroconductive gel is used to sense the ECG signals from the patient.

FIG. 14 illustrates an example of a defibrillator electrode pad/paddle 202a, 202b with the patient-facing surface covered by a microneedle array wherein FIG. 15 illustrates an example of a defibrillator electrode pad/paddle with an outer circumference of its patient-facing surface covered by a microneedle array and the center without microneedles where electroconductive gel is used to sense the ECG signals from the patient. FIG. 16 illustrates an example of a defibrillator electrode pad/paddle with a majority of the patient-facing surface covered by a microneedle array and the central channels without microneedles where electroconductive gel is used to sense the ECG signals from the patient and FIG. 17 illustrates an example of a defibrillator electrode pad/paddle with the patient-facing surface covered by a microneedle array and regions without microneedles where electroconductive gel is used to sense the ECG signals from the patient.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A defibrillator, comprising:
   two paddles for delivering a shock to a patient;
   each paddle having a microneedle array with two or more rows of conductive microneedles;
   a device for generating a therapeutic current to deliver the shock to the patient through the two paddles, wherein the device has at least a battery and a capacitor and is partially incorporated within the paddles; and
   wherein the microneedle array of the two paddles applies a voltage and causes electroporation of a skin surface of the patient and delivers the shock to the patient through the skin surface.

2. The defibrillator of claim 1, wherein each microneedle in the microneedle array has the same shape.

3. The defibrillator of claim 1, wherein each microneedle in the microneedle array has a different shape.

4. The defibrillator of claim 1, wherein each microneedle in the microneedle array has a cylindrical shape.

5. The defibrillator of claim 1, wherein each microneedle in the microneedle array has a pyramidal shape.

6. The defibrillator of claim 5, wherein each pyramidal shaped microneedle further comprises one more portions that extend from a surface of the pyramidal shaped microneedle to increase an effective surface area of the pyramidal shaped microneedle.

7. The defibrillator of claim 1, wherein each microneedle in the microneedle array has one of a prism shape, a curved blade shape and a C-channel shape.

8. The defibrillator of claim 1, wherein each paddle has the microneedle array around an outer circumference of the paddle.

9. The defibrillator of claim 1, wherein the microneedle array is a first quadrant of microneedles, a second quadrant of microneedles, a third quadrant of microneedles and a fourth quadrant of microneedles wherein the four quadrants are separated from each other.

10. The defibrillator of claim 1, wherein the microneedle array is at least a first quadrant of microneedles and a second quadrant of microneedles wherein the quadrants are separated from each other.

11. The defibrillator of claim 1, wherein each microneedle is constructed from one of a pharmaceutical grade stainless steel, gold, titanium, nickel, iron, gold, platinum, tin, chromium, copper, alloys, silicon, silicon dioxide, capacitive carbon, graphite and polymers.

12. The defibrillator of claim 1, wherein each microneedle is constructed from a biocompatible material.

13. The defibrillator of claim 1 further comprising an impedance sensor that measures a depth of skin surface penetration of the microneedles.

14. A method for reducing patient transthoracic impedance for the purpose of delivering a therapeutic current, the method comprising:
   providing a microneedle array having two or more rows of microneedles;
   performing electroporation of a skin surface of the patient by applying a voltage using the microneedle array;
   puncturing one or more layers of the skin surface using the microneedle array; and
   delivering a therapeutic current and a shock through the skin surface of the patient using the microneedle array at a reduced power due to a reduced transthoracic impedance caused by the electroporation and/or the microneedles.

15. The method of claim 14 further comprising determining, using an impedance sensor, a depth of penetration in the skin surface of the microneedles.

* * * * *